United States Patent [19]

Kreisher et al.

[11] Patent Number: 4,622,124
[45] Date of Patent: Nov. 11, 1986

[54] DEVICE FOR HORIZONTAL ELECTROBLOTTING

[75] Inventors: John H. Kreisher, Ridgefield; Thomas L. McCarthy, Cheshire, both of Conn.

[73] Assignee: International Biotechnologies, Inc., New Haven, Conn.

[21] Appl. No.: 690,649

[22] Filed: Jan. 11, 1985

[51] Int. Cl.$^4$ ............................................. G01N 27/28
[52] U.S. Cl. .............................. 204/301; 204/299 R; 204/182.8
[58] Field of Search .............. 204/299 R, 301, 180 G, 204/182.8

[56] References Cited

PUBLICATIONS

Biorad Laboratories, "Chromatography Electrophoresis Immunochemistry and HPLC", Jan. 1982, pp. 125-127 and 138-139.
Gershoni, J. M., et al., "Protein Blotting: Principles and Applications", Analytical Biochemistry, vol. 131, pp. 1-15 (1983).
Gibson, W., "Protease-Facilitated Transfer of High-Molecular-Weight Proteins During Electrotransfer to Nitrocellulose", Analytical Biochemistry, vol. 118, pp. 1-3 (1981).
McLellan, T., et al, "Serial Electrophoretic Transfers: A Technique for the Identification of Numerous Enzymes from Single Polyacrylamide Gels", Biochemical Genetics, vol. 19, pp. 647-654 (1981).
Towbin, H., et al, "Electrophoretic Transfer of Proteins from Polyacrylamide Gels to Nitrocellulose Sheets: Procedure and Some Applications", Proceedings of the National Academy of Science, USA, vol. 76, pp. 4350-4353 (1979).

Primary Examiner—John F. Niebling
Assistant Examiner—B. J. Boggs, Jr.
Attorney, Agent, or Firm—Bachman & LaPointe

[57] ABSTRACT

A device for the horizontal electroblotting of electrophoretically transferred material comprising a fluid tight container having a floor, a lid and side walls extending between the floor and the lid for defining a chamber, a support assembly located in the chamber for supporting the material to be electroblotted, a first electrode provided below the support assembly and a second electrode provided above the support assembly and a barrier provided in the chamber between the first electrode and the support assembly for diverting bubbles produced by the first electrode so as to prevent the bubbles from accumulating on the support assembly during the electroblotting of the electrophoretically transferred material.

10 Claims, 6 Drawing Figures

DEVICE FOR HORIZONTAL ELECTROBLOTTING

BACKGROUND OF THE INVENTION

Electrophoresis, in general, is the phenomenon of the migration of charged particles or ions in a liquid carrier medium under the influence of an electric field. This phenomenon can be used to separate small particles which, by reasons of different surface chemical properties, exhibit different concentrations of surface charge in the given medium. Under the influence of the electrical field, the electrophoretic mobilities of the various classes of charged particles in the carrier medium will be different. A sample introduced at some point into the sheet of liquid carrier medium (buffer) diffuses slowly in a narrow band in the absence of a potential gradient; however, when the potential gradient is applied to the sheet of buffer, the sample particles are separated under the influence of the electrical field into various particle groups or components depending upon the electrophoretic mobility of the respective particles, the strength of the field, and the length of time that the particles remain in the field. Particles of similar mobility are concentrated in distinctive zones or bands at defined distances from the point of sample introduction (origin).

Blotting or transfer of electrophoretically resolved material, such as DNA, RNA, and protein, has become a standard procedure when sensitive and specific detection of biologically interesting macromolecules is required.

Electroblotting offers significant advantages over capillary blotting in that the electroblotting procedure is much quicker. Capillary transfer and electroblotting both require that the gel be placed in contact with the paper or other membrane to which the proteins or nucleic acids or other materials will be transferred. The difference between the methods is the transfer driving force. In capillary transfer the driving force is the absorptive potential of the filter paper, or other material. The transfer material, e.g., nitrocellulose or nylon, is placed between the gel and the absorptive paper. In electroblotting, however, as currently practiced the gel and transfer material are vertically suspended in a buffer tank between two electrodes. The protein or nucleic acids are thus driven out of the gel onto the transfer material using electrical potential. For example, a typical system involves placing a nylon membrane against a gelatin sheet, submerging the gel-nylon assembly vertically into a buffer solution, then applying an electric potential transversely across the assembly using the buffer solution as the conducting medium. This system typically uses two platinum wire electrodes, one on each side of a gel-nylon combination, and establishes a voltage gradient in the buffer solution. The electrodes are laid out in grid fashion and spaced at a distance from the gel and nylon to obtain a reasonably uniform electric field using the least amount of platinum.

The blotting procedure offers significant advantages. Firstly, molecules in the matrix of a gel are relatively inaccessible to probes such as antibodies. Transfer to the surface of a membrane allows analyses that are difficult or impossible in the gel. Also, since the transferred molecules are located at or near the surface of the membrane, analysis time is substantially reduced. In addition, the membranes are relatively strong and easy to handle in contrast to the gels which are easily torn. Moreover, the transferred molecules are bound to the membrane so that there is no loss of resolution while biological activity is usually retained. Thus, storage of the membrane prior to use is usually feasible.

As mentioned hereinabove, in electroblotting as currently practiced the gel and transfer material are vertically suspended in a buffer tank between two electrodes. A number of disadvantages are associated with vertical electroblotting. For example, battery jar-type tanks limit the size of the gel blot possible while blotting tanks for blotting large electrophoresis gels require excessive amounts of buffer and are very expensive to construct. In addition, holders for vertical blotting systems must be very strong to maintain close proximity of the gel and blotting membrane. This requires large support systems which tend to block the electrical charge thereby leading to blurred blots. The size of the support system also limits the size of the gel blot possible. Finally, soft agarose gels, such as those required for genome identification, cannot be blotted in a vertical electroblotting system due to the slippage, sliding and collapsing of the gel in the support holder.

Attempts at horizontal blots, which would overcome some of the problems noted above with regard to vertical blotting systems, have been largely unsuccessful. During electroblotting in horizontal blotting systems oxygen and hydrogen bubbles are created at the cathode and anode respectively during electrolysis. The bubbles given off at the electrode beneath the horizontally disposed gel membrane accumulate on the lower surface of the membrane thereby partially blocking the electrical charges which results in uneven blotting.

Naturally, it would be highly desirable to provide a horizontal electroblotting system suitable for use with soft agarose gels and the like wherein bubbles which are created at the electrodes during electrolysis are dispersed in such a manner as to prohibit accumulation of bubbles on the undersurface of the horizontally disposed gel membrane.

Accordingly, it is the principal object of the present invention to provide a device for the horizontal electroblotting of electrophoretically transferred material.

It is a further object of the present invention to provide a device as aforesaid which is particularly suitable for use with soft gels such as agarose gels and the like.

It is a particular object of the present invention to provide a device as aforesaid which prevents accumulation of bubbles on the undersurface of the horizontally disposed gel membrane.

It is a still further object of the present invention to provide a device as aforesaid which is of simple construction, economic to manufacture and easily used in electroblotting.

Further objects and advantages of the present invention will appear hereinbelow.

SUMMARY OF THE INVENTION

In accordance with the present invention the foregoing objects and advantages are readily obtained.

The present invention relates to a device for the electroblotting of electrophoretically transferred material and, more particularly, a device for horizontal electroblotting. The device of the present invention comprises a liquid tight container having a support assembly horizontally disposed in a chamber defined by the container. A first electrode is provided below the support assembly and a second electrode is provided above the support assembly. The electrodes are typically platinum;

however electrodes made of carbon or other conductive material could be employed. A bubble diverting barrier is provided between the first electrode and the support assembly for diverting bubbles produced by the first electrode so as to prevent the bubbles from accumulating on the undersurface of the support assembly which would result in uneven blotting. The support assembly comprises first and second support surfaces which are clamped together for clamping the gel and absorbent receptor membrane together. As a result of the horizontal disposition of the support surfaces little compression is required to hold the gel and membrane in contact thus allowing for the use of very dilute soft gels.

The device of the present invention offers significant advantages over the procedures used heretofore. Firstly, horizontally disposed electroblotting type systems are inherently easier to use than a vertical system. Significantly, the device of the present invention allows for the use of soft, dilute gels without the worry of slippage which occurs in vertical electroblotting systems. Finally, the device of the present invention insures even blotting by eliminating bubble accumulation on the undersurface of the gel support assembly during the electroblotting process. Thus, it can be readily seen that the device of the present invention offers significant advantages which, heretofore, have not been obtained in prior art devices.

Further advantages of the present invention will appear hereinafter.

DETAILED DESCRIPTION

Figure 1:
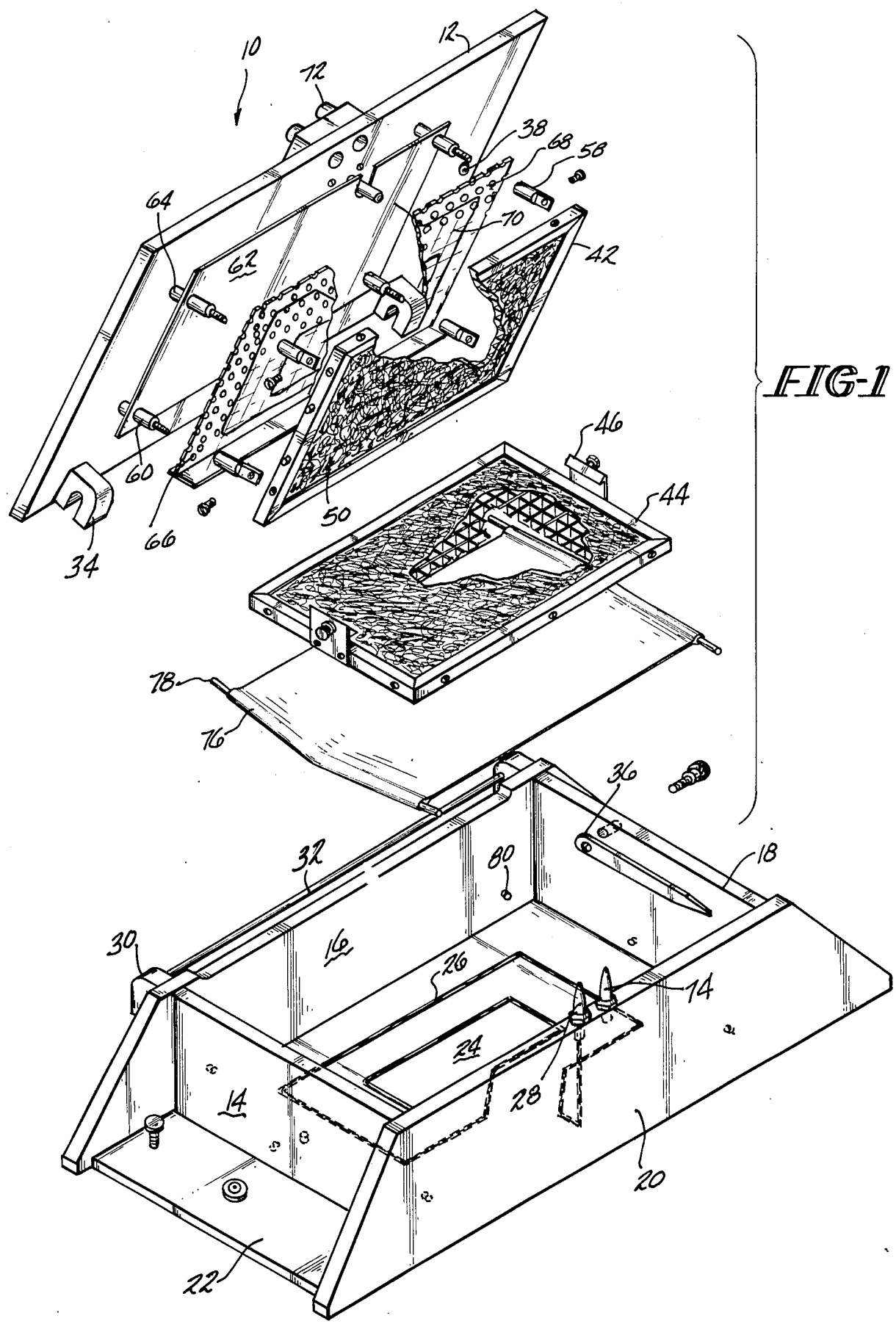
FIG. 1 is a partially exploded view in perspective of an electroblotting device in accordance with the principles of the present invention.
Figure 2:
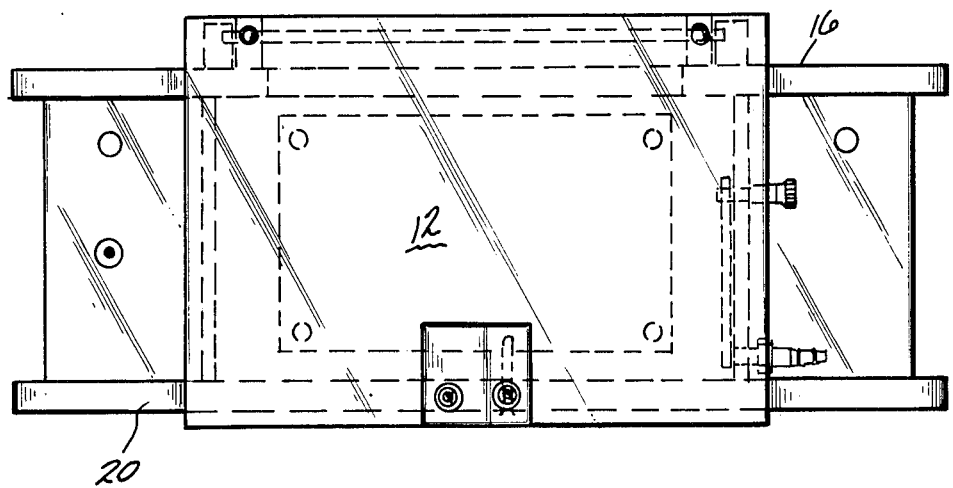
FIG. 2 is a top plane view of the device of the present invention.

Referring in detail to the drawings, the horizontal electroblotting device 10 comprises a fluid tight container having a lid 12, side walls 14, 16, 18 and 20, respectively and a floor 22 which define a chamber 24. The floor 24 is provided with an electrode 26 which extends into side wall 20 where it is connected to an electrical connector 28. Side wall 16 has a pair of posts 30 which receives a rod 32 which is received in U-shaped clips 34 provided on the underside of lid 12. Side wall 18 is provided with a pivotably rotating lever 36 which in one position is adapted to be received in dimple 38 provided in the lid 12 for holding the lid in the open position as shown in FIG. 5.

Figure 3:
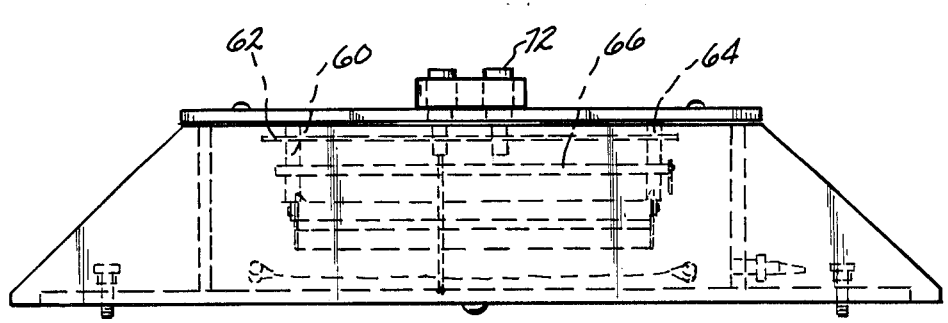
FIG. 3 is a front elevation of the device of FIG. 2.
Figure 4:
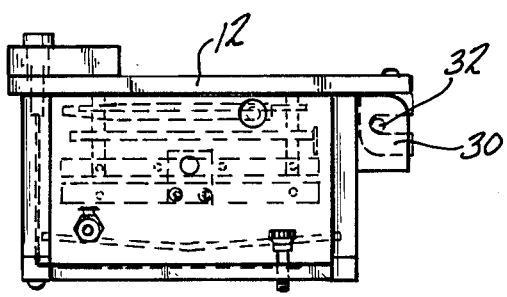
FIG. 4 is an elevational view of the right side of FIG. 2.
Figure 5:
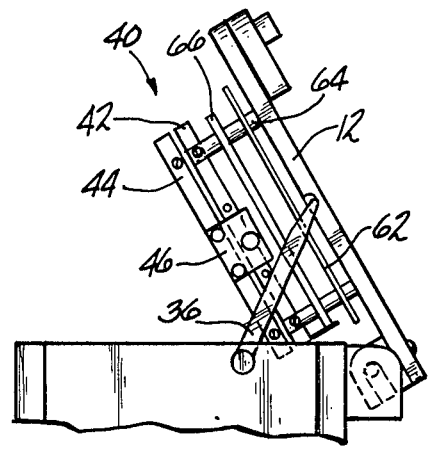
FIG. 5 is a partial elevational view of the right side of FIG. 2 illustrating the lid in its open position.
Figure 6:
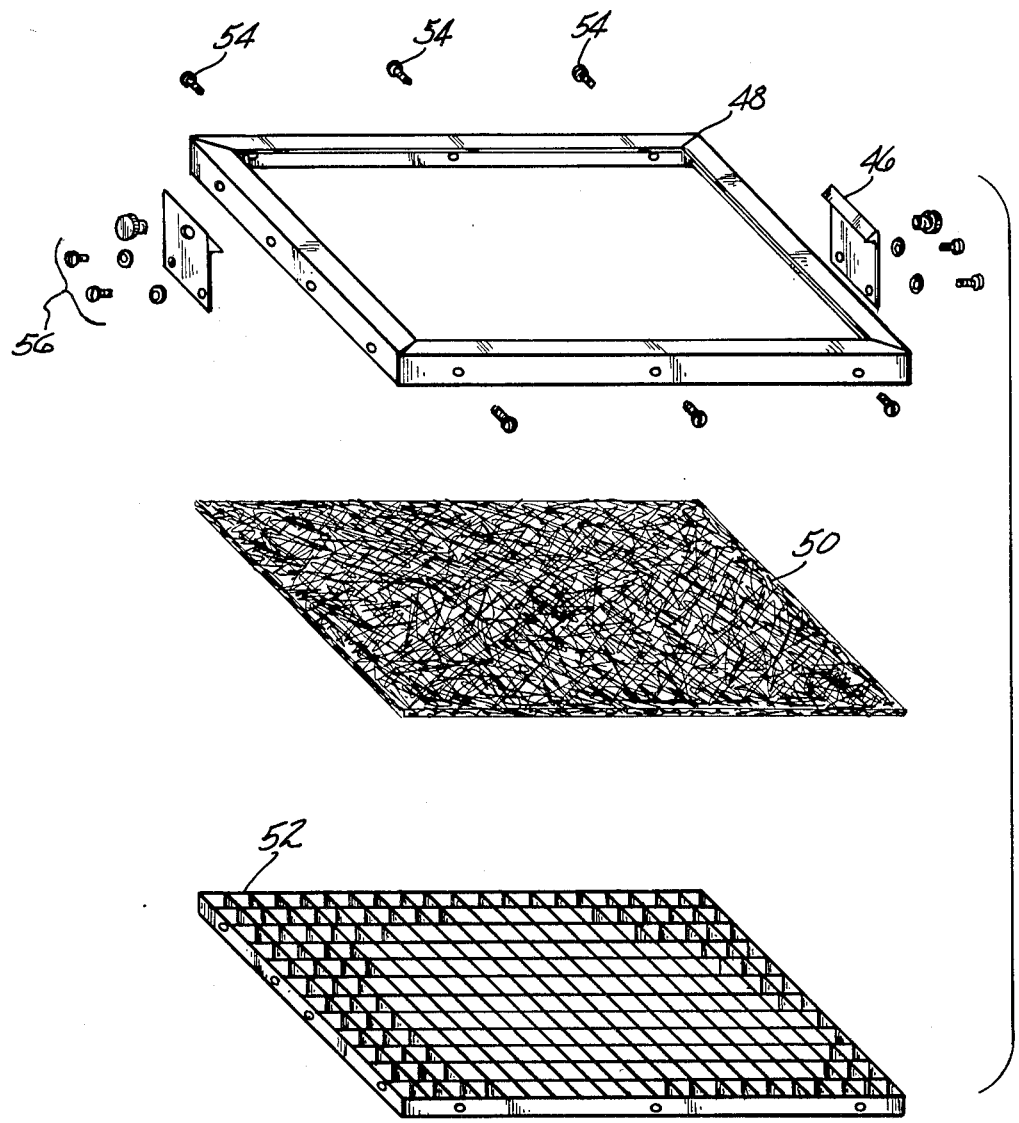
FIG. 6 is an exploded view in perspective of the lower support surface of the support assembly employed in the device of the present invention.

A support assembly indicated generally by the reference numeral 40 in FIG. 5 is suspended from lid 12 in chamber 24 when lid 12 is in its closed position as shown in FIGS. 3 and 4. The support assembly comprises a first upper support surface assembly 42 and a second lower support surface assembly 44 which are held together by clamps 46 provided on lower support surface assembly 44. As can best be seen in FIG. 6 each of the support surface assemblies 42 and 44 comprises a frame 48 having a mat 50 mounted in the frame and held in place by a backing plate 52 by means of screws 54. As noted above the lower support surface assembly is provided with clamps 46 which are mounted to the frame 48 by suitable screws and nuts 56. In accordance with the present invention the mat 50 comprises a porous material such as that sold under the trademark SCOTCH-BRITE sold by the 3M Company. A suitable material is the General Purpose Scotch-Brite Layer Number 7447. The backing plate 52 is preferably an egg crate arrangement which allows for the buffer solution to pass therethrough and penetrate the mat 50. The backing plate must have sufficient rigidity to insure an even compression of the mat within the frame 48.

The support assembly 40 is suspended from lid 12 by means of posts 58 which threadably receive screw posts 60. The screw posts 60 are glued to a heat barrier plate 62 which is in turn spaced from the lid 12 by means of posts 64. Provided between the heat barrier plate 62 and the support assembly 40 is a honey-comb plate 66 having holes 68 therein. The screw posts 60 pass through the holes 68 and are secured to the posts 58 for holding the honey-comb plate 66 in place. A second electrode 70 is provided on the honey-comb plate 66 and passes up to ferrule 72 provided on the top of lid 12 where it makes contact with an electrical contact which is adapted to make electrical contact with connector 74 when the lid is in its closed position.

In accordance with the present invention a nylon screen 76 is provided in the chamber between the first electrode 26 in the floor 24 and the support assembly 40 suspended from the lid 12 for diverting bubbles produced in the buffer solution between first electrode 26 to the sides of the chamber so as to prevent bubbles from accumulating on the undersurface of the support assembly 40 during the electroblotting of the electrophoretically transfer material. In accordance with the present invention the nylon screen 76 (or a screen made of another suitable material) should have a size and shape which is at least substantially the same as that of the support assembly 40 so as to insure that the bubbles are diverted to the sides of the chamber in such a manner so as to prohibit accumulation on the support assembly 40. The screen 76 is mounted on a pair of V-shaped poles 78 such that the screen 76 forms a slight angle with respect to the floor 24 of the container so as to aid in leading the bubbles off to the side of the container. It has been found that an angle of about ¼" per 4 inches of horizontal exposure is ideal in leading off the bubbles. The screen 76 is held in place within the chamber by mounting the poles 78 in blind bores 80 provided in the walls 16 and 20 respectively of the container.

The horizontal electroblotting device of the present invention operates in the following manner. The lid 12 of the horizontal unit containing the support assembly 40 and the electrode 70 mounted on honey-comb plate 66 is removed from the device and laid upside down on the work area. Support surface assembly 44 is removed by bending out the clips 46. The gel to be used is placed on the mat 50 of the support surface assembly 42. Support surface assembly 44 is then clamped back in place so as to sandwich the gel between the support surface assemblies 42 and 44. The lid is then hinged to bar 32 and closed so as to immerse the support assembly 40 in the buffer solution provided in chamber 44. Electrical contact is made between the electrodes 26 and 70 by the electrical connectors 28 and 74 and DC current of approximately 50 to 150 volts is applied for a period of 3 to 5 hours. At the completion of the run, the sandwich assembly is opened and the nylon transfer membrane removed.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A device for the horizontal electroblotting of electrophoretically transferred material comprising a fluid tight container having a floor, a lid and side wall means extending between said floor and said lid for defining a chamber, a support assembly located in said chamber for supporting the material to be electroblotted, a first electrode provided below said support assembly and a second electrode provided above said support assembly and means provided in said chamber between said first electrode and said support assembly for diverting bubbles produced by said first electrode so as to prevent said bubbles from accumulating on said support assembly during the electroblotting of the electrophoretically transferred material wherein said means provided in said chamber between said first electrode and said support assembly comprises a membrane disposed in said chamber and spaced from said floor such that said membrane is disposed at an angle with respect to said floor.

2. A device according to claim 1 wherein said means provided in said chamber between said first electrode and said support assembly for diverting bubbles has a shape and surface area substantially identical to the shape and surface area of said support assembly.

3. A device according to claim 1 wherein said support assembly is mounted on said lid.

4. A device according to claim 1 wherein a screen is provided between said second electrode and said lid for dissipating heat produced by said second electrode.

5. A device according to claim 4 wherein said second electrode is mounted on a porous support.

6. A device according to claim 1 wherein said first electrode is provided in said floor.

7. A device according to claim 1 wherein said support assembly comprises a upper support surface and a lower support surface and means for clamping said upper support surface to said lower support surface.

8. A device according to claim 7 wherein each of said upper support surface and said lower support surface comprises a frame, a mat provided in said frame and a backing plate for supporting said mat in said frame.

9. A device according to claim 8 wherein said mat is porous.

10. A device according to claim 1 wherein said membrane is substantially V-shaped and has a pair of legs which are disposed at an angle with respect to said floor.

* * * * *